US00PP09022P

United States Patent [19]

Wuhl

[11] Patent Number: Plant 9,022

[45] Date of Patent: Dec. 27, 1994

[54] PRIMETIME PLUM TREE

[76] Inventor: Eric Wuhl, 5480 E Lane Ave., Fresno, Calif. 93727

[21] Appl. No.: 174,802

[22] Filed: Dec. 29, 1993

[51] Int. Cl.[5] ..... A01H 5/00

[52] U.S. Cl. ..... Plt./38.1

[58] Field of Search ..... Plt. 38.1

*Primary Examiner*—James R. Feyrer

*Attorney, Agent, or Firm*—Worrel & Worrel

[57] ABSTRACT

A new and distinct variety of plum tree which is somewhat remotely similar to the Eldorado plum tree, but from which it is distinguished by producing uniformly larger fruit of a heart-shaped form having a distinct flavor and which are mature for harvesting and shipment approximately the same time as that of the "Eldorado" plum tree, but which exhibit a superior holding ability as compared with the fruit of the "Eldorado" plum tree.

1 Drawing Sheet

BACKGROUND OF THE NEW VARIETY

The present invention relates to a new and distinct variety of plum tree, which will hereinafter be denominated varietally as the "Primetime" plum tree, and more particularly to a plum tree which produces a firm, uniformly large fruit having a distinct flavor and which are mature for commercial harvesting and shipment approximately the first week of July in the San Joaquin Valley of central California.

The commercial appeal of tree fruit may be based upon one or more attributes. Characteristically, commercially successful tree fruit possesses noteworthy attributes in several significant categories. Among the more significant categories are flavor, keeping quality size, shape and skin coloration. The relative importance of these categories may appear evident. However, in reality, the very subjective nature of the evaluation in several key areas renders an overall evaluation subjective to some degree. Thus, for example, the appeal of the flavor of free fruit may largely be dependent upon personal preference.

As a consequence, distinctive attributes in the more objective categories such as size, shape and skin coloration are often very important to the commercial success of tree fruit. In this regard, typically the larger the size of the fruit, the greater the commercial appeal. The same may be said for tree fruit having a uniformly distinctive shape and an intense skin coloration. It is unusual to find a variety of tree fruit possessing exemplary attributes in a number of these more objective categories. The fruit of the new variety of plum tree of the present invention is noteworthy in impressive array of these more objective categories.

ORIGIN AND ASEXUAL REPRODUCTION OF THE NEW VARIETY

The present variety of plum tree was discovered by the inventor in 1985, as one of 35 seedlings found in his orchard in Fresno, Calif., which was planted in the varieties 'Challenger' (unpatented) and 'Showtime', U.S. Plant Pat. No. 8,037. Because this tree expresses traits of each of these two trees and has some expressions which are intermediate other traits of both trees, it is believed that this tree is an F1 hydrid of the varieties, 'Challenger' and 'Showtime'. The new variety was selected from thirty-five (35) seedlings. The new variety was asexually reproduced at the inventor's direction in 1987 by budding onto "Nemaguard" rootstock in Fresno County in June of that year. The resulting asexually reproduced trees were planted in an orchard located on the inventor's property in Fowler, Calif. These trees have been observed by the inventor since that time and he has confirmed that the distinctive characteristics of the parent tree of the new variety are in all respects reproduced in its progeny.

SUMMARY OF THE NEW VARIETY

The "Primetime" plum tree is characterized by producing very firm, uniformly large fruit which have a slight reddish coloration becoming a very dark eggplant color when fully mature and which are ripe for commercial harvesting and shipment approximately the first week of July in the San Joaquin Valley of central California. The new variety is somewhat remotely similar to the "Eldorado" plum tree, but is distinguished therefrom in that the fruit of the new variety are larger and heart-shaped. The fruit is clingstone with flesh having an outstanding, sweet flavor and a reddish coloration and exceptional keeping quality.

BRIEF DESCRIPTION OF THE DRAWING

The drawing is a color photograph showing mature fruit of the new variety of plum tree of the present invention including a first shown in plan view showing the apex end thereof; a second shown in side elevation to illustrate the distinctive heart shape thereof; a third sectioned and laid open with the stone left in place in one section and the stone removed to expose the pit cavity in the other section; a fourth shown in side elevation; a fifth shown in plan view showing the base end thereof; representative foliage of the new variety; and a stone thereof.

DETAILED DESCRIPTION

Referring more specifically to the pomological details of this new and distinct variety of plum tree, the following has been observed under the ecological conditions prevailing at the orchard of origin which is located in Fresno County, Calif. All major color code designations are by reference to the *Dictionary of Color*, by Maerz and Paul, Second Edition, 1950, and *Color, Universal Language and Dictionary of Name*, by Kelly and Judd, 1976. Common color names are also occasionally employed.

TREE

Generally:

*Size.*—Medium. Trees are only four (4) to five (5) years old. Potential tree size is large. The amount of terminal growth attained in one growing season is from 1.82 m (6.01 ft) to 2.74 m (9.04 ft).

*Vigor.*—Moderate vigor, upright growth.

*Chilling requirements.*—Approximately 800 hours below 45 degrees Fahrenheit. Similar to other plum varieties.

*FIG.*—Trees were trained in accordance with a special system — modified leader to improve production.

*Productivity.*—Highly productive.

*Regularity of bearing.*—Regular.

*Internode length.*—Approximately 30 mm (1.181 inches).

Trunk:

*Size.*—Medium. Measurement not taken because the trees are not yet fully mature.

*Surface texture.*—Rough with epidermal cells peeling off in a regular pattern.

*Color.*—Page 53, Plate 15, 11-A or 12-A, coffee or burnt umber of Maerz and Paul.

Lenticels.—Numbers — Numerous. Size — Small, 1 mm to 2 mm (0.039 inches–0.079 inches) to medium, 3 mm to 5 mm (0.118 inches–0.197 inches), slightly elongated.

Branches:

*Size.*—Medium to large.

*Growth habit.*—Upright. Angle of scaffold branches to the central leader is seventeen degrees (17°) to eighty-five degrees (85°).

*Density.*—Open and sprawling. Develops whips.

*Surface texture.*—Mature — Rough, similar to trunk. Immature — smooth with intact epidermal cells. None peeling off.

*Color.*—One year or older wood — Similar to trunk; that is, Page 53, Plate 15, 11-A, or 12-A, coffee or burnt umber, of Maerz and Paul. Immature branches — Page 65, Plate 21, 2-C of Maerz and Paul. Number 103, d.g.y. dark green yellow olive, of Kelly and Judd.

*Lenticels.*—Generally — Variable depending upon age of branch. Numbers — Young shoots — Very few. Numbers — Mature or older wood — Several. Size — Variable small, 1 mm to 2 mm (0.039 inches–0.079 inches) to medium, 3 mm to 5 mm (0.118 inches–0.197 inches).

LEAVES

Size:

*Generally.*—Medium to large depending upon age. Data hereafter is for mature leaves.

*Average length.*—100.6 mm±1.6 mm (4.1 inches±0.06 inches).

*Average width.*—49.6 mm±2.0 mm (2.0 inches±0.08 inches).

Form: Ranges from lanceolate to ovate to obovate.

Base.—Acute.

*Apex.*—Acuminate.

Color:

*Upwardly disposed surface—mature leaves.*—Page 69, Plate 23, J-7 or J-8, elm or Mt. Vernon green, of Maerz and Paul. Number 125, medium olive green, to number 138, very dark yellow green, of Kelly and Judd.

*Downwardly disposed surface—mature leaves.*—Page 67, Plate 22, I-5 or J-5, sage green or leek green, of Maerz and Paul. Number 120, medium yellow green, of Kelly and Judd.

*Upwardly disposed surface—immature leaves.*—Page 67, Plate 22, K-6, cress green, of Maerz and Paul. Number 120, medium yellow green, of Kelly and Judd.

*Downwardly disposed surface—immature leaves.*—Page 67, Plate 22, K-6, cress green, of Maerz and Paul. Number 120, medium yellow green, of Kelly and Judd.

Marginal form.:

*Generally.*—Mostly serrulate, some leaves show a fine serrate margin.

Leaf vein:

*Form.*—Pt. Palmate.

*Color.*—Same as remainder of leaf.

*Thickness.*—Thin.

Glandular characteristics: Not always present. None on immature leaves. One or two on mature leaves.

Glands:

*Location.*—Opposite and alternate.

*Color.*—Green.

*Shape.*—Globose.

*Size.*—Small.

Petiole:

*Size.*—Generally — Small to medium.

*Length.*—15.7 mm±0.7 mm (0.64 inches±0.03 inches).

*Thickness.*—1.8 mm±0.1 mm (0.07 inches-0.004 inches).

*Color.*—immature leaves.—Page 41, Plate 9, F-8, slightly reddish, of Maerz and Paul.

*Color—mature leaves.*—Page 59, Plate 18, J-4, green, of Maerz and Paul.

Stipules: Two small, but well defined stipules are present at base of each leaf.

FLOWERS

Flower buds: *Size.*—Small, tender, conic in shape and short. Description is based on current season growth.

*Surface texture.*—Smooth.

Date of bloom: Popcorn stage, February 18; First bloom, February 20; Fifty-percent bloom, February 25; Full bloom, February 28; Petal fall, March 1.

Petals:

*Color.*—White.

*Size.*—Approximately 20 mm (0.79 inches).

*Showiness.*—Very showy.

Stamens:

*Numbers.*—Numerous.

Pollen:

*Color.*—Golden.

*Quantity.*—Medium.

Self-fertility level: Semi-self fruitful.

FRUIT

Maturity when described: Ripe for commercial harvesting and shipment approximately the first week of July in the San Joaquin Valley of central California. Later harvest by July 7 to 8 in area of Fresno, Calif.

Size:

*Generally.*—Very large, uniform in size, shape and weight.

*Light thinning.*—Separate fruit in clusters.

*Average diameter in the axial plane.*—66.8 mm±1.6 mm (2.7 inches±0.06 inches).

*Average diameter transverse in the suture plane.*—63.5 mm±0.8 mm (2.57 inches±0.03 inches).

*Average diameter transverse and at right angles to the suture plane.*—66.8 mm±1.2 mm (3.34 inches±0.05 inches).

Weight:

*Range.*—From 116 grams to 198 grams.

*Average.*—147.5 grams±4.0 grams (5.2 ounces±0.14 ounces). Three (3) fruit≅1.0 pounds.

Form:

*Uniformity.*—Very uniform. Most of the fruit are cordate (heart shaped) with a slightly pointed tip, typical of cordate form. Few have a more rounded apex.

*Symmetry.*—Symmetrical.

Suture:

*Generally.*—A very shallow, inconspicuous line extends from the base to the apex and is slightly deep at cavity.

Ventral surface:

*Generally.*—Smooth, rounded.

Stem cavity:

*Generally.*—Almost round shape, flaring.

*Width.*—16.1 mm±1.3 mm (0.65 inches±0.05 inches).

*Depth.*—Shallow, 8.5 mm±0.6 mm (0.34 inches±0.02 inches).

*Length.*—Round shape, slightly elongated.

*Shape.*—Flaring with a slight elongation in suture plane.

Stem:

*Generally.*—Medium short.

*Caliper—length.*—15.5 mm±0.8 mm (0.63 inches±0.03 inches).

*Caliper—diameter.*—2.4 mm±0.1 mm (0.1 inches±0.004 inches).

Apex: Shape - Mammiform.

Pistil point - Position - Apical.

Skin:

*Thickness.*—Thin, adheres strongly to flesh.

*Texture.*—Tender.

*Flavor.*—No bitter taste.

*Tendency to crack.*—Rare, if any at all. None seen in the field.

*Color.—general.*—Mature fruit show a slight reddish color, but fully mature (ripe) show a very dark eggplant color.

*Blush color.*—Page 105, Plate 41, 8-L, of Maerz and Paul.

*Ground color.*—Page 119, Plate 48, H, or J-12, eggplant, of Maerz and Paul. Number 260, deep purple red, of Kelly and Judd.

Flesh:

*Flesh color.*—Mixture of yellow/red. Page 109, Plate 43, G-1, rhodonite pink, of Maerz and Paul. Number 30, very deep yellow pink, of Kelly and Judd. Most of the flesh is translucent light yellowish red with red/pink veins, or vascular strands, that diffuse throughout the flesh.

*Color of pit well.*—Page 47, Plate 12, F-10, caramel color, of Maerz and Paul.

*Juice production.*—Juicy, but no free-flowing juice.

*Flavor.*—Sweet, excellent, good balance between sugar and acid, distinct flavor, delicate.

*Aroma.*—Pronounced aroma.

*Texture.*—Firm, crisp, very pleasing.

*Fibers—numbers.*—Few, short, branched throughout the flesh.

*Fibers—texture.*—Soft.

*Ripening.*—Even ripening throughout the fruit.

*Eating quality.*—Excellent flavor and texture. No bitter aftertaste.

Stone:

*Attachment.*—Cling. Flesh adheres to pit, particularly along dorsal and ventral sides, but relatively free on the sides (semi-free).

*Fibers—numbers.*—Very few along the ventral and dorsal sides. *Fibers—length.*—Medium ranges from 2 mm (0.079 inches) to 5 mm (0.197 inches).

*Size—generally.*—Medium.

*Size—length.*—26.6 mm±0.8 mm (1.08 inches±0.03 inches).

*Size—width.*20.4 mm±0.4 mm (0.8 inches±0.02 inches).

*Size.*—Thickness.—9.5 mm±0.3 mm (0.3 inches±0.01 inches).

*Form.*—Generally—oblong.

*Apex.*—Shape—Pointed, acute.

*Color.*—Dry — page 45, Plate 11, K-10, orange yellow, of Maerz and Paul. Number 68, slightly orange yellow, of Kelly and Judd.

*Base.*—Shape—flat, narrow.

*Sides.*—Generally — flat to slightly curved with few shallow ridges along the dorsal and ventral sides.

*Tendency to split.*—None.

Keeping quality: Excellent. Fruit is very firm at maturity and when ripe. Remained very firm after two weeks of cool storage.

Resistance to disease: Average. No known resistance or unusual susceptibility to known insects or diseases. Tolerates heat well with no signs of sunburn.

Shipping and handling qualities: Excellent. The fruit holds well on the tree and will ship and store very well after harvest.

Although the new variety of plum tree possesses the described characteristics noted above as a result of the growing conditions prevailing near Fresno in the central portion of the San Joaquin Valley of California, it is to be understood that variations of the usual magnitude and characteristics incident to changes in growing conditions, irrigation, fertilization, pruning, pest control, climatic variation and the like are to be expected.

Having thus described and illustrated my new variety of plum tree, what I claim as new and desire to be secured by Plant Letters Patent is:

1. A new and distinct variety of plum tree substantially as illustrated and described which is somewhat remotely similar to the "Eldorado" plum tree, but from which it is distinguished by producing uniformly larger, heart-shaped fruit having a very firm flesh with a distinct sweet flavor and which are mature for commercial harvesting and shipment approximately the first week of July in the San Joaquin Valley of central California.

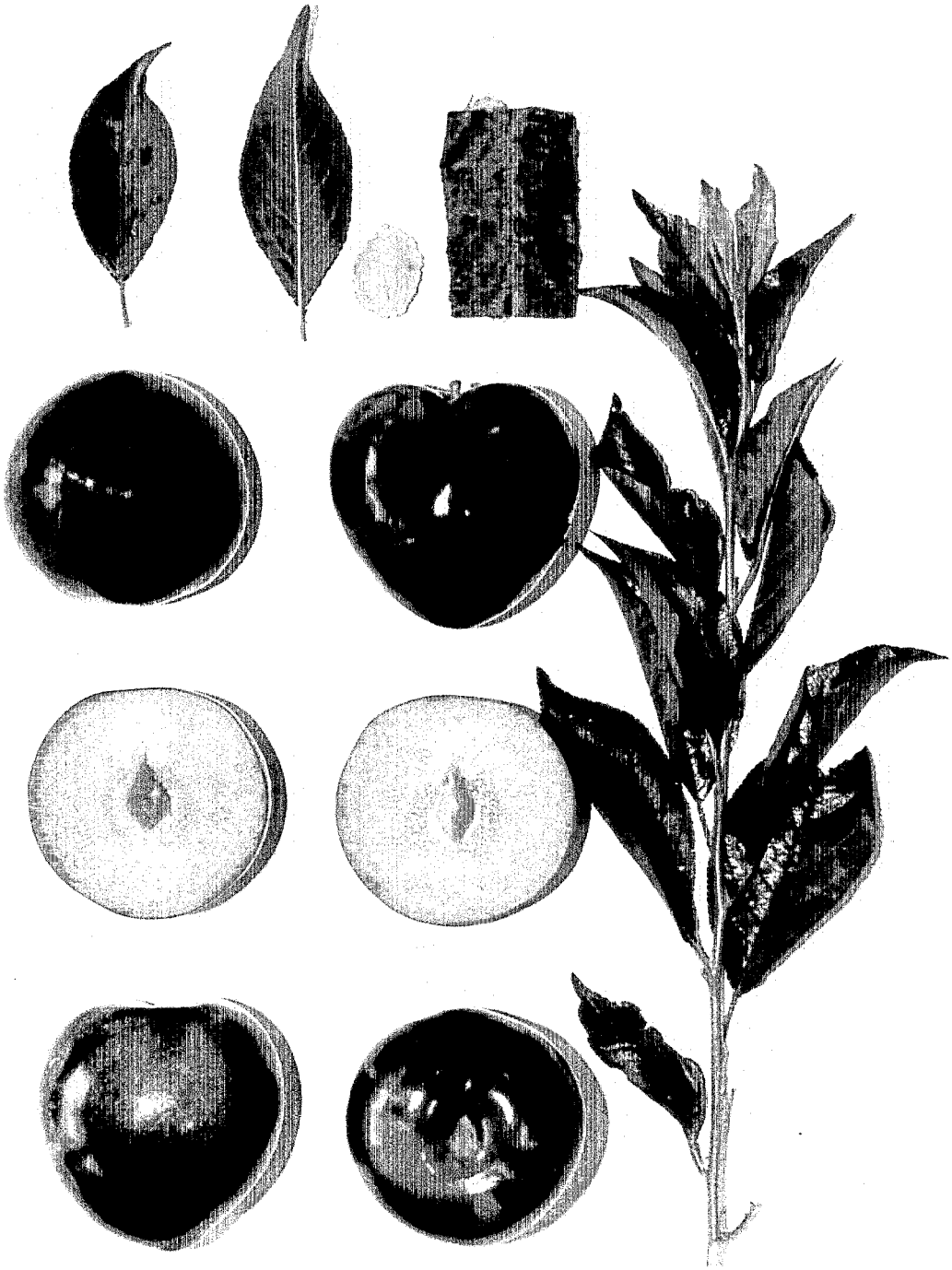

* * * * *